US012023265B2

(12) United States Patent
Gilmartin et al.

(10) Patent No.: US 12,023,265 B2
(45) Date of Patent: Jul. 2, 2024

(54) STENT INCLUDING ANTI-MIGRATION CAPABILITIES

(71) Applicant: BOSTON SCIENTIFIC SCIMED, INC., Maple Grove, MN (US)

(72) Inventors: Gary Gilmartin, Foxford (IE); Geraldine Toner, Raphoe (IE); Daniel Tuck, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 569 days.

(21) Appl. No.: 16/743,049

(22) Filed: Jan. 15, 2020

(65) Prior Publication Data
US 2020/0222212 A1 Jul. 16, 2020

Related U.S. Application Data

(60) Provisional application No. 62/793,178, filed on Jan. 16, 2019.

(51) Int. Cl.
*A61F 2/82* (2013.01)
*A61L 31/08* (2006.01)
*A61L 31/10* (2006.01)

(52) U.S. Cl.
CPC ............... *A61F 2/82* (2013.01); *A61L 31/10* (2013.01); *A61F 2220/0008* (2013.01);
(Continued)

(58) Field of Classification Search
CPC ............... A61F 2/82; A61F 2220/0008; A61F 2250/0025; A61F 2230/0071;
(Continued)

(56) References Cited

U.S. PATENT DOCUMENTS 5,201,766 A * 4/1993 Georgette ........... A61F 2/30767
623/923
5,330,500 A 7/1994 Song
(Continued)

FOREIGN PATENT DOCUMENTS

| EP | 2033667 A2 * | 3/2009 | ............... A61F 2/82 |
| WO | 9907308 A1 | 2/1999 | |
| WO | WO-2011024831 A1 * | 3/2011 | ............... A61F 2/82 |

OTHER PUBLICATIONS

Bando et al. translation of WO2011/024831 (Year: 2011).*
International Search Report and Written Opinion dated Apr. 29, 2020 for International Application No. PCT/US2020/013613.

*Primary Examiner* — Brian E Pellegrino
(74) *Attorney, Agent, or Firm* — Seager, Tufte & Wickhem, LLP

(57) ABSTRACT

An example medical device for treating a body lumen is disclosed. The medical device includes an expandable scaffold including a first end region, a second end region opposite the first end region and an outer surface. The medical device also includes a covering disposed along the outer surface of the expandable scaffold, the covering having an outer surface. The medical device further includes a plurality of granular particles disposed along the covering. Additionally, the expandable scaffold is configured to shift from a collapsed state to an expanded state, the covering is configured to contact an inner surface of the body lumen in the expanded state and the granular particles are designed to prevent migration of the expandable scaffold upon implantation in the body lumen.

16 Claims, 11 Drawing Sheets

(52) U.S. Cl.
CPC ............... *A61F 2250/0025* (2013.01); *A61F 2250/0036* (2013.01); *A61L 2400/18* (2013.01)

(58) Field of Classification Search
CPC .... A61F 2002/30838; A61F 2210/0076; A61F 2250/0067; A61F 2/06; A61L 31/08; A61L 2400/18; A61L 31/082; A61L 2420/08; Y10S 977/931
See application file for complete search history.

(56) References Cited

U.S. PATENT DOCUMENTS

| | | |
|---|---|---|
| 9,034,456 B2 | 5/2015 | Nielson et al. |
| 9,439,790 B2 | 9/2016 | Clerc et al. |
| 2004/0039438 A1* | 2/2004 | Alt ..................... A61L 31/082 623/1.39 |
| 2004/0052859 A1 | 3/2004 | Wu et al. |
| 2004/0211362 A1 | 10/2004 | Castro et al. |
| 2006/0193892 A1 | 8/2006 | Furst et al. |
| 2008/0319540 A1 | 12/2008 | Jordan et al. |
| 2013/0268063 A1 | 10/2013 | Firstenberg et al. |
| 2014/0277395 A1 | 9/2014 | Firstenberg et al. |
| 2015/0051693 A1 | 2/2015 | Bertolino et al. |
| 2016/0317330 A1 | 11/2016 | Clerc et al. |
| 2017/0252144 A1 | 9/2017 | Hannon et al. |
| 2018/0193175 A1 | 7/2018 | Bluecher et al. |

\* cited by examiner

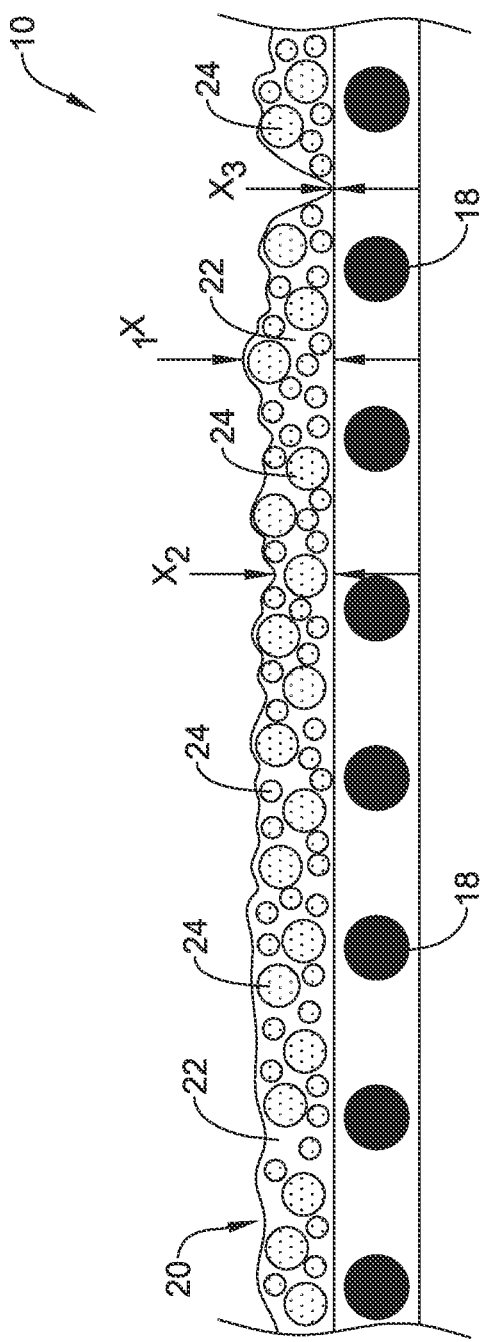
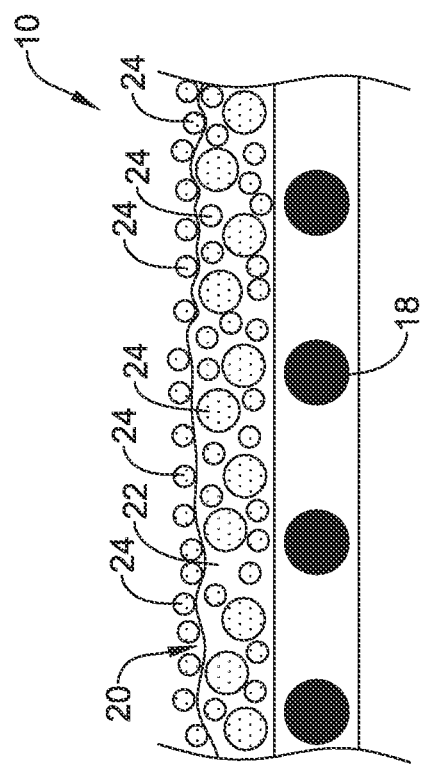
FIG. 2
FIG. 2A

STENT INCLUDING ANTI-MIGRATION CAPABILITIES

CROSS-REFERENCE TO RELATED APPLICATIONS

This application claims the benefit of priority under 35 U.S.C. § 119 of U.S. Provisional Application No. 62/793,178 filed Jan. 16, 2019, the entire disclosure of which is hereby incorporated by reference.

TECHNICAL FIELD

The present disclosure pertains to medical devices, and methods for manufacturing medical devices. More particularly, the present disclosure pertains to examples of expandable stents having anti-migration capabilities and methods for manufacturing and using such devices.

BACKGROUND

Implantable medical devices (e.g., expandable stents) may be designed to treat strictures in a body lumen and/or provide a fluid pathway for digested material, blood, or other fluid to flow therethrough following a medical procedure. Some medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design stents to include sufficient flexibility while maintaining sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth into the interstices or openings thereof. The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). However, covered stents may be more prone to migration than bare stents (as discussed above). Therefore, in some instances it may be desirable to design a stent which includes a covered portion having anti-migration capabilities. Examples of medical devices anti-migration capabilities are disclosed herein.

BRIEF SUMMARY

This disclosure provides design, material, manufacturing method, and use alternatives for medical devices. An example medical device for treating a body lumen includes an expandable scaffold including a first end region, a second end region opposite the first end region and an outer surface. The medical device also includes a covering disposed along the outer surface of the expandable scaffold, the covering having an outer surface. The medical device further includes a plurality of granular particles disposed along the covering. Additionally, the expandable scaffold is configured to shift from a collapsed state to an expanded state, the covering is configured to contact an inner surface of the body lumen in the expanded state and the granular particles are designed to prevent migration of the expandable scaffold upon implantation in the body lumen.

Alternatively or additionally to any of the embodiments above, wherein the plurality of granular particles are encapsulated within the covering.

Alternatively or additionally to any of the embodiments above, wherein at least some of the granular particles are disposed along the outer surface of the covering.

Alternatively or additionally to any of the embodiments above, wherein the plurality of granular particles includes a first microbead.

Alternatively or additionally to any of the embodiments above, wherein the first microbead includes a first outer diameter, and wherein the first outer diameter is between 0.50 mm and 0.90 mm.

Alternatively or additionally to any of the embodiments above, wherein the first microbead is spherically-shaped.

Alternatively or additionally to any of the embodiments above, further comprising a second microbead, and wherein the second microbead extends radially outward from the outer surface of the expandable scaffold a greater distance than the first microbead extends from the outer surface of the expandable scaffold.

Alternatively or additionally to any of the embodiments above, wherein the plurality of granular particles are arranged to create a surface texture having a variable surface roughness.

Alternatively or additionally to any of the embodiments above, wherein the covering includes a first thickness and a second thickness different from the first thickness.

Alternatively or additionally to any of the embodiments above, wherein the first end region, the second end region or both the first end region and the second end region include a flared portion.

Alternatively or additionally to any of the embodiments above, wherein the covering is disposed along the entire outer surface of the expandable scaffold.

Alternatively or additionally to any of the embodiments above, wherein the covering is disposed only along a portion of the outer surface of the expandable scaffold.

Alternatively or additionally to any of the embodiments above, wherein the expandable scaffold includes a plurality of interstices located therein, and wherein the covering spans at least one of the plurality of interstices.

Another medical device for treating a body lumen includes an expandable scaffold including a first end region, a second end region opposite the first end region and an outer surface. The medical device also includes a covering disposed along the outer surface of the expandable scaffold and a plurality of microbeads disposed along the covering. Additionally, the plurality of microbeads are disposed along the covering to form a variable surface texture and the covering is configured to contact an inner surface of the body lumen such that the plurality of microbeads prevent migration of the expandable scaffold upon implantation in the body lumen.

Alternatively or additionally to any of the embodiments above, wherein the plurality of microbeads are encapsulated within the covering.

Alternatively or additionally to any of the embodiments above, wherein some of the plurality of microbeads include a first outer diameter, and wherein the first outer diameter is between 0.50 mm and 0.90 mm.

Alternatively or additionally to any of the embodiments above, wherein at least some of the plurality of microbeads are spherically-shaped.

Alternatively or additionally to any of the embodiments above, wherein the plurality of microbeads includes a first microbead and a second microbead, and wherein the second microbead extends radially outward from the outer surface of the expandable scaffold a greater distance than the first microbead extends from the outer surface of the expandable scaffold.

Alternatively or additionally to any of the embodiments above, wherein the covering includes a first thickness and a second thickness different from the first thickness.

A method of manufacturing a medical stent includes applying a covering to an outer surface of an expandable scaffold, wherein the covering includes a coating and a plurality of microbeads. Applying the covering to the outer surface of the expandable scaffold includes applying a first layer of the coating material onto the outer surface of the expandable scaffold, disposing a plurality of microbeads onto the first layer of coating material and applying a second layer of the coating material onto the first layer of the coating material and the plurality of microbeads such that the plurality of mircobeads are encapsulated between the first layer of coating material and the second layer of the coating material.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 2 illustrates a detailed view of a portion of the stent shown in FIG. 1;

FIG. 2A illustrates a detailed view of another portion of the stent shown in FIG. 1;

Figure 1:
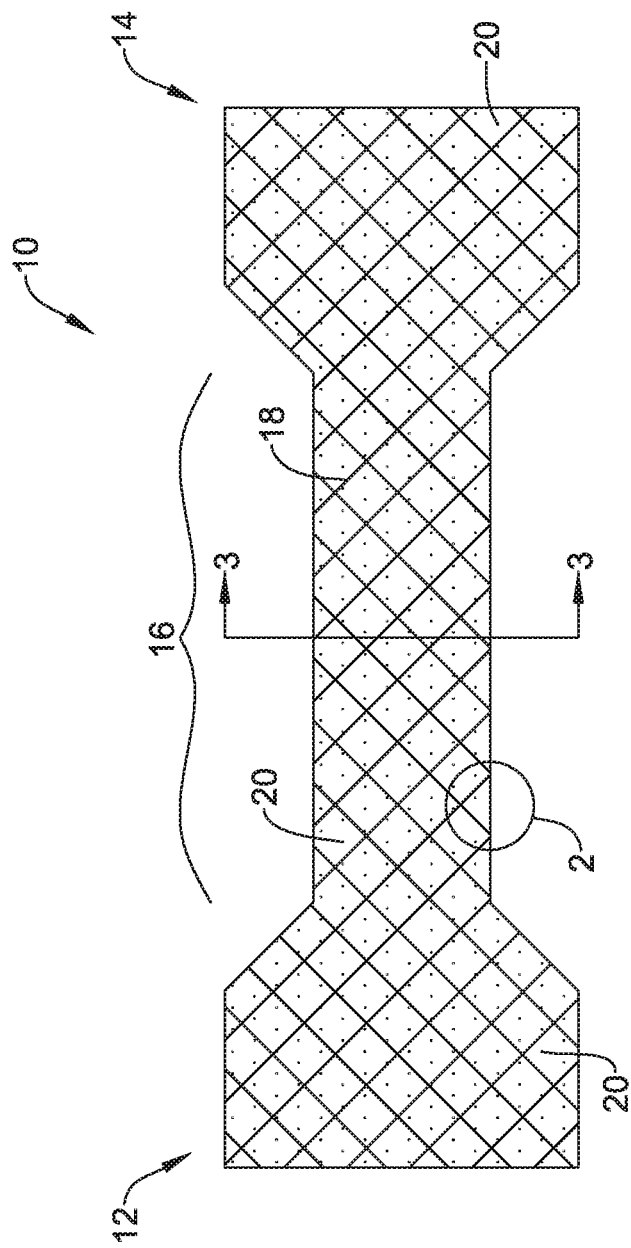
FIG. 1 illustrates an example stent including a covered region.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, implantable medical devices may be designed to treat strictures in a body lumen and/or provide a fluid pathway for digested material, or other material or fluid, to flow therethrough following an invasive medical procedure. Examples disclosed herein may include radially or self-expanding stents. The expandable stents may be implanted transluminally via an endoscope, or another desired delivery means. Additionally, some stents may be implanted in a variety of body lumens such as the esophageal tract, the gastro-intestinal tract including the intestine and the colon, airways, urinary tracts, biliary tract including bile and/or pancreatic ducts, vascular system, etc.

In some instances, it may be desirable to design stents to include sufficient flexibility to be able to conform to the tortuous body lumen during delivery yet sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophagus or intestine may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). One method to reduce stent migration while maintaining the ability to remove and/or reposition the stent may include designing the outer surface of the stent to include an anti-migration surface texture. For example, a stent scaffold may include a gripping structure that improves the surface friction of the stent. The increased surface friction may anchor the stent in place and reduce the risk of stent migration. Example medical devices including an anti-migration surface texture are disclosed below.

FIG. 1 illustrates an example implantable medical device, illustrated as a stent 10. However, although illustrated as a stent, the implantable medical device 10 may be any of a number of devices that may be introduced endoscopically, subcutaneously, percutaneously or surgically to be positioned within an organ, tissue, or lumen, such as an intestine, colon, urethra, esophagus, trachea, bronchus, bile duct, blood vessel, or the like. The stent 10 may be configured to be positioned in a body lumen for a variety of medical applications. For example, the stent 10 may be used to treat a stricture in a body lumen. Additionally, the stent 10 may be used to provide a pathway for food or other digested materials to pass therethrough without directly contacting adjacent tissue. It is contemplated that the examples described herein may be utilized in the gastrointestinal tract, as well as in the esophageal, vascular, urinary, biliary, tracheobronchial, or renal tracts, for example. In some instances, the stent 10 (e.g., an intestinal stent, an esophageal stent, a vascular stent, tracheal stent, bronchial stent, etc.) may include an expandable scaffold.

The expandable scaffold of stent 10 may have a first end region 12 and a second end region 14 positioned on an opposite end of the stent 10 from the first end region 12. In some instances, the first end region 12 may extend to a first end of the implantable medical device 10 and the second end region 14 may extend to a second end of the implantable medical device 10 opposite the first end. The first end region 12 may be attached to the second end region 14 along a medial region 16 of the implantable medical device 10 to form an expandable tubular framework or scaffold with open ends and defining a lumen extending therein. As shown in FIG. 1, the first end region 12 and/or the second end region 14 may include a flared portion, if desired. For example, FIG. 1 illustrates both the first end region 12 and the second end region 14 having an outer diameter that is greater than the outer diameter of the medial region 16.

A plurality of strut members 18 may be arranged in a variety of different designs and/or geometric patterns to form the expandable tubular framework or scaffold of the stent 10. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 18 combined to form a rigid and/or semi-rigid stent structure. In some examples disclosed herein, the collection of strut members 18 forming a rigid and/or semi-rigid framework structure may be referred to as a scaffold. For example, the strut members 18 may be wires or filaments braided, intertwined, interwoven, weaved, knitted, crocheted or the like to form the expandable scaffold or framework of the stent 10. The strut members (e.g., wires or filaments) 18 of the stent 10 may be configured to self-expand to an expanded diameter when unconstrained. Alternatively, the strut members 18 may be formed from a monolithic structure (e.g., a cylindrical tubular member), such as a single, cylindrical tubular laser-cut Nitinol tubular member, in which the remaining portions of the tubular member form the strut members 18. The monolithic structure of the stent 10 may be configured to self-expand to an expanded diameter when unconstrained.

The expandable scaffold of stent 10 in at least some examples disclosed herein may be constructed from a variety of materials. For example, the expandable scaffold of the stent 10 may be constructed from a metal (e.g., Nitinol). In other instances, the expandable scaffold of the stent 10 may be constructed from a polymeric material (e.g., PET). In yet other instances, the expandable scaffold of stent 10 may be constructed from a combination of metallic and polymeric materials. Additionally, the expandable scaffold of stent 10 or portions thereof may include a bioabsorbable and/or biodegradable material.

As discussed above, in some instances it may be desirable to design the stent 10 to include a covering composition, including a plurality of discrete components, such as particles of a first material dispersed or encapsulated within a coating of a material. For example, FIG. 1 shows stent 10 including a covering composition 20 (indicated by the dotted pattern in FIG. 1) disposed along an outer surface of the expandable scaffold of the stent 10. While FIG. 1 illustrates the covering composition 20 extending along the entire length of the stent 10, in some examples, the covering composition 20 may be disposed along only a portion of the stent 10. Example stent designs including a covered portion and an uncovered portion will be discussed below with respect to FIGS. 5-9.

FIG. 2 illustrates a detailed view of a portion of the example stent 10 shown in FIG. 1. In particular, FIG. 2 illustrates a portion of the expandable scaffold including struts 18 and the covering composition 20 described above. For example, FIG. 2 illustrates the covering composition 20 (e.g., covering, coating, etc.) positioned on and/or adjacent to the outer surface of the strut members 18. Additionally, FIG. 2 illustrates that the covering composition 20 may include a plurality of granular particles 24 (e.g., discrete granules) disposed along and/or within a coating 22. The granular particles 24 may be embedded within the coating 22, such as being embedded between a first layer of the coating (radially inward of the granular particles) and a second layer of the coating (radially outward of the granular particles). In some instances, the individual granular particles 24 may be referred to as a microbead or a plurality of microbeads 24.

In some instances, the coating 22 may include an elastomeric or non-elastomeric material. Further, a portion of the coating 22 may be formed from a suitable material, such as a biostable material. For example, the coating layer 22 may include a polymeric material, such as silicone, polytetrafluoroethylene, polyurethane, or the like, or other materials including those disclosed herein. Further, a portion of the coating 22 may be a biostable material. For purposes of discussion herein, a biostable material may be defined as a material that does not biodegrade. For example, the coating 22 may include a polymeric material, such as silicone, polytetrafluoroethylene, polyurethane, or the like, or other materials including those disclosed herein.

As shown in FIG. 2, the microbeads 24 may be substantially spherical-shaped. However, it is contemplated that the microbeads 24 may include triangular, square, ovular, rectangular or any other suitable geometric shape. Additionally, the plurality of microbeads 24 may all be include a single shape (e.g., all the microbeads 24 may be spherical-shaped), or alternatively, the microbeads 24 may include a combination of different shapes (e.g., some microbeads 24 may be spherical-shaped and some may be ovular-shaped).

Furthermore, it can be appreciated that each of the microbeads 24 may include an outer diameter. FIG. 2 illustrates that the plurality of microbeads 24 may include microbeads 24 having different outer diameters. For example, some of the microbeads 24 may have a larger diameter that other microbeads 24. However, in other examples, the plurality of microbeads 24 may have a uniform outer diameter. In other words, each of the plurality of microbeads 24 may have similar outer diameters. In such cases, the outer diameter of each microbead 24 may be about 0.01 mm to 1.5 mm, or about 0.1 to about 1.2 mm, about 0.2 to about 1.0 mm, or about 0.4 to about 0.8 mm, or about 0.7 mm.

The microbeads 24 described above may be formed from a variety of materials. For example, the individual microbeads 24 may be formed from any biocompatible material, including, but not limited to, rigid or semi-rigid materials, PTFE, PET, ceramics, metals (e.g., Nitinol, stainless steel), etc. Other example materials are listed below.

Further, in some examples, the microbeads 24 may be formed from a material which hardens over a time period. For example, the microbeads 24 may be formed from a material that hardens with moisture absorption over time, such that the microbeads 24 are soft on the tissue of a body lumen upon initial deployment of the stent 10, but harden over time to increase the security of the stent 10 as healing of the body lumen occurs. In yet other examples, the microbeads 24 may include a drug coating. The drug coating may be placed on an outer surface of the individual microbeads 24, whereby the drug coating is designed to dissolve through the coating material 22 over a time period. In this example, a solid core of the microbeads 24 may remain along the coating material 22 to maintain the security of the stent 10 over time. Additionally, as will be discussed in greater detail below, the microbeads 24 may be formed from a material that expands over time and/or when exposed to a stimulus.

FIG. 2 further illustrates that, in some examples, the individual microbeads 24 may be encased (e.g., encapsulated) within the coating 22. In other words, in some examples, each of the plurality of microbeads 24 may be surrounded (e.g., encased) by the coating material 22, such as between a first layer of the coating material 22 and a second layer of the coating material 22. However, in other examples, one or more of the microbeads 24 may be positioned along the outer surface of the coating 22, as shown in FIG. 2A. In other words, in some examples, some of the microbeads 24 may be positioned within the coating 22 while some of the microbeads 24 may be attached along the outer surface of the coating material 22. In these examples, it is contemplated that a portion of the microbeads 24 positioned along the outer surface of the coating 22 may extend radially outward of an outer surface of the coating 22, with a portion of the outer surface of the microbeads exposed from the coating 22, as shown in FIG. 2A. In yet other examples, it is contemplated that all of the microbeads 24 may be positioned along the outer surface of the coating 22.

As discussed above, FIG. 2 shows the example covering composition 20 disposed along the strut members 18. The covering composition 20 may fully cover the stent 10, thus extending across or spanning the interstices between struts 18 of the expandable framework of scaffold of stent 10. While FIG. 2 shows the covering composition 20 extending along the outer surface of strut members 18, it is contemplated that coating assembly may extend along the inner surface of strut members 18 and/or may fully surround one or more of the strut members 18.

Further, FIG. 2 illustrates the covering composition 20 may be disposed along the strut members 18 such that the covering composition 20 is positioned radially outward of the strut members 18 and may extend across the interstices or openings between adjacent struts 18. In other words, the covering composition 20 may be arranged such that the covering composition 20 is on the outer surface of strut members 18 of the stent 10 to fully cover the stent 10, and thus prevent tissue ingrowth into the stent 10. Further, FIG. 2 illustrates that the covering composition 20 may be positioned at an outermost surface of the stent 10 such that it contacts the inner surface of a body lumen in which the stent 10 may be deployed.

As shown in FIG. 2, in some examples, one or more of the microbeads 24 may extend radially away from the outer surface of the expandable scaffold of the stent 10 a greater distance than one or more other microbeads 24. For example, one or more adjacent microbeads 24 may "stack" on top of one another within and/or along the coating 22. It can be appreciated that the stacking of the microbeads 24 may result in the covering composition 20 to include a variable thickness. For example, FIG. 2 illustrates that the covering composition 20 may include a first thickness $X_1$ and a second thickness $X_2$, whereby the thickness $X_1$ is greater that the thickness $X_2$. It can be appreciated that the variable thickness of the covering composition 20 may result in the coating assembly to have a textured and/or a roughened surface 23 designed to contact and engage with the inner surface of an example body lumen engaged therewith. For example, in some instances, textured surface may temporarily anchor the covered portion of stent 10 along the inner surface of an example body lumen. Additional examples of the textured surface and its method of use will be described in greater detail below.

Additionally, it is contemplated that in some examples, the covering composition 20 may include portions which do not include any microbeads 24. In other words, the covering composition 20 may include regions which include a space between adjacent microbeads 24. For example, FIG. 2 illustrates a third thickness $X_3$ which defines a region along the covering composition 20 in which a gap may exist between adjacent microbeads 24. It can be appreciated from FIG. 2 that the diameter $X_3$ may define a location in which no microbeads 24 are stacked on top of one another. Further, the diameter $X_3$ may only include the thickness of the coating 22.

Figure 3:
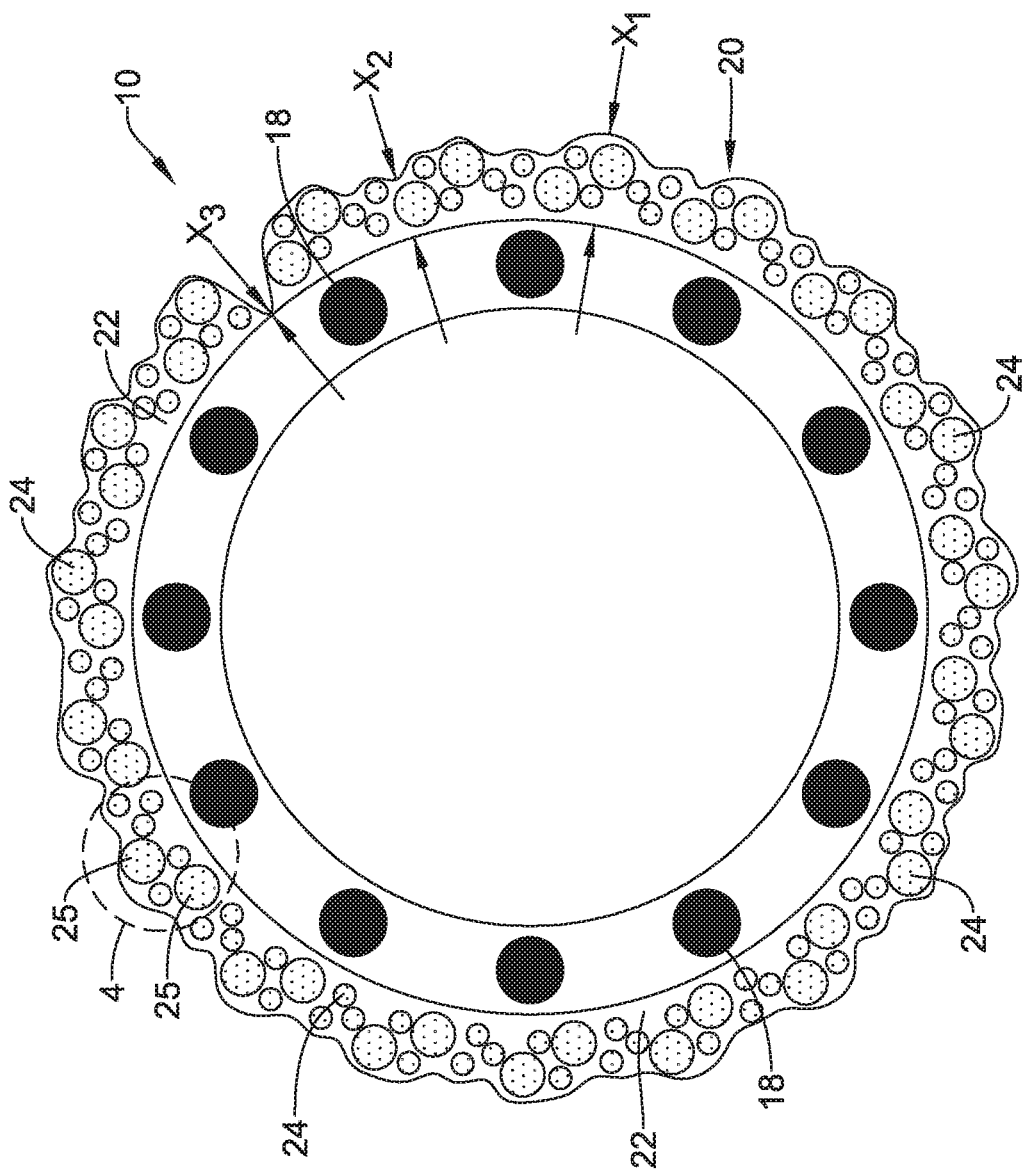
FIG. 3 illustrates a cross-sectional view along line 3-3 of the stent shown in FIG. 1.

FIG. 3 illustrates a cross-section taken along line 3-3 of FIG. 1. FIG. 1 illustrates the stent 10 including the covering composition 20 and the stent struts 18 making up the expendable scaffold of the stent 10. Further, FIG. 3 illustrates that covering composition 20 extending radially away from the outer surface of the stent struts 18. As described above, FIG. 3 further illustrates the plurality of microbeads 24 positioned along a coating material 22. As shown in FIG. 3, the plurality of microbeads are encapsulated in the coating material 22. In other words, the coating material 22 covers the entire surface of each of the plurality of microbeads 24. Additionally, FIG. 3 shows the covering composition 20 having the first thickness $X_1$, the second thickness $X_2$ and the third thickness $X_3$. As discussed above, these variable thicknesses may create a surface texture which increases the surface friction between the coating assembly and an inner surface of a body lumen, thereby improving the anti-migration capabilities of the stent 10.

Figure 4:
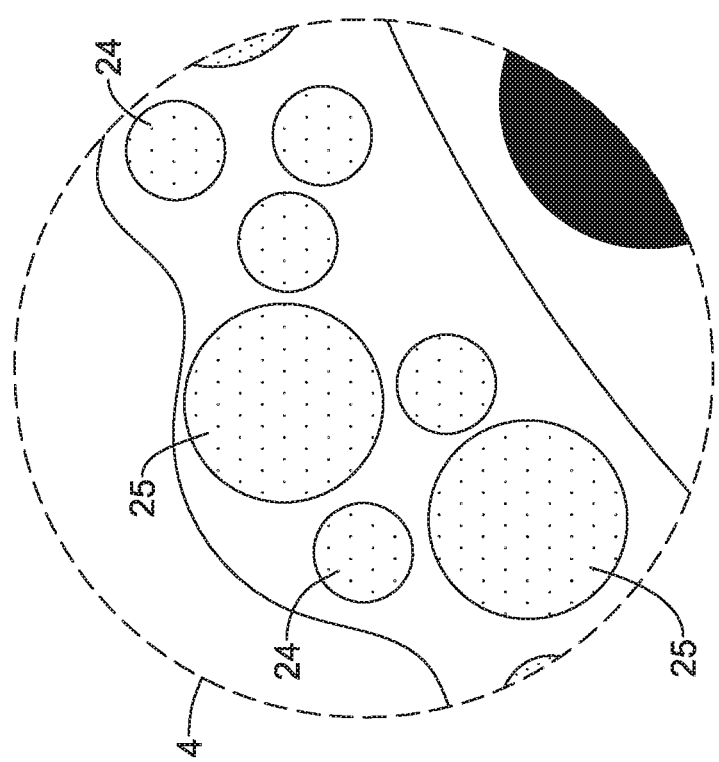
FIG. 4 illustrates a detailed view of a portion of the stent shown in FIG. 3.

Additionally, as discussed above, FIG. 3 illustrates that in some examples the microbeads 24 may include one or more microbeads 24 having variable diameters. For example, FIG. 3 illustrates a microbead 25 having a diameter which is larger than other microbeads 24 positioned adjacent to the microbead 25. FIG. 4 illustrates a detailed view of FIG. 3 to further illustrate the difference in diameter of the microbead 25 as compared to the adjacent microbeads 24. As illustrated, the diameter of the microbead 25 is larger than the adjacent microbeads 24.

Figure 5:
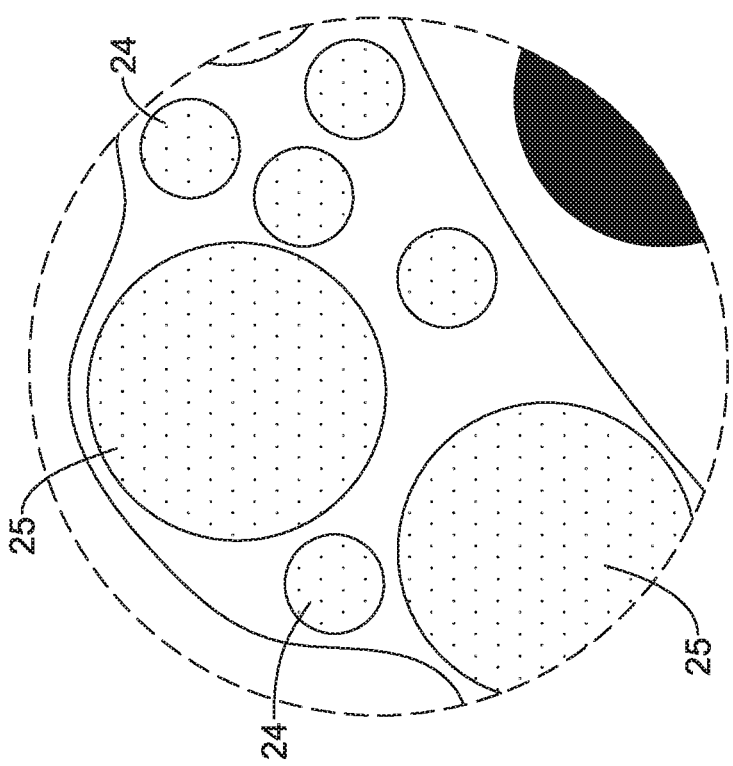
FIG. 5 illustrates another detailed view of a portion of the stent shown in FIG. 3.
Figure 6:
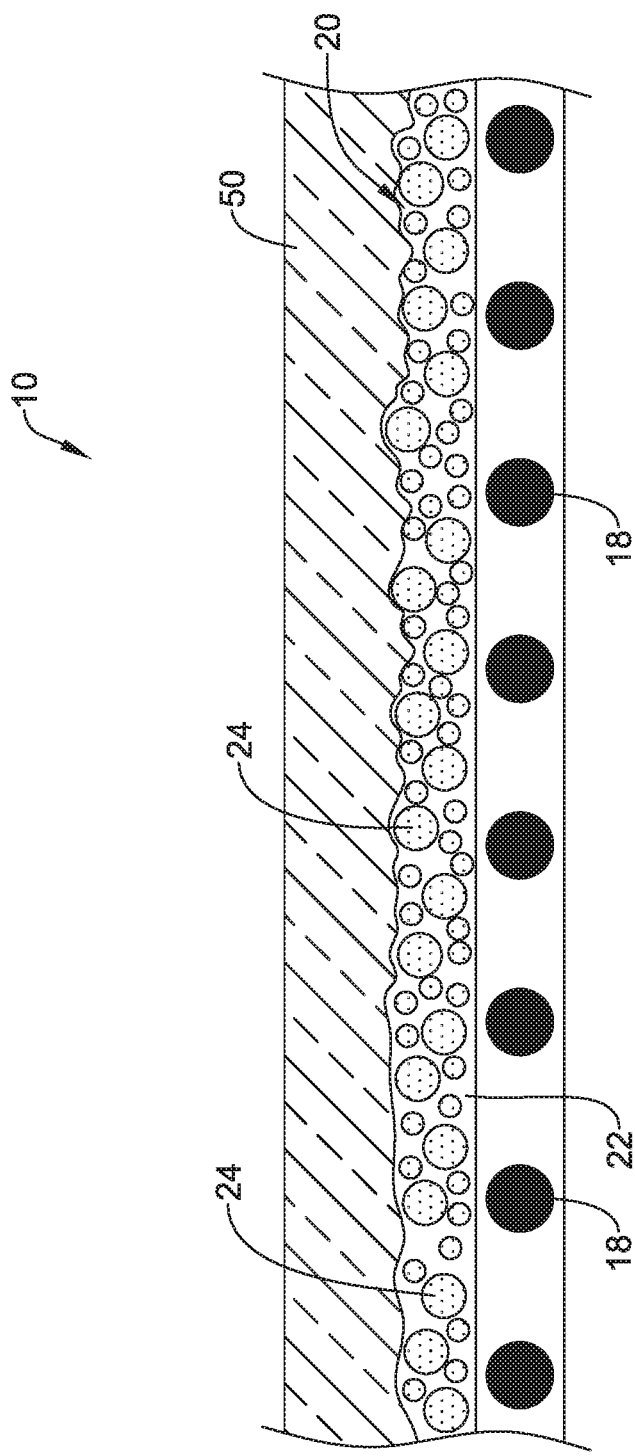
FIG. 6 illustrates the example stent shown in FIG. 1 deployed in a body lumen.

As discussed above, in some examples it may be desirable to design one or more of the microbeads 24 to expand (e.g., enlarge, grow, swell, etc.) over time and/or when exposed to a stimulus. It can be appreciated that, in some examples, one or more of the microbeads 24 may be designed to expand in the presence of a fluid (e.g., water, saline, etc.). FIG. 5 illustrates the detailed view of the stent 10 shown in FIG. 4 whereby the microbeads 25 may have absorbed a fluid and expanded to a diameter which is larger than the diameter of the microbeads 25 depicted in FIG. 4. It can be appreciated that expanding the microbeads 25 to a larger diameter may create increased variability in the surface texture of the covering composition 20 described above.

As discussed above, it can be appreciated that the covering composition 20 (including the microbeads 24 positioned within the coating 22) described above may be configured to prevent stent 10 from shifting longitudinally or migrating relative to an inner surface of a body lumen when stent 10 is positioned adjacent a target site (e.g., when placed adjacent in the esophagus or intestine). In some instances, the roughened surface of the covering composition 20 may include a variety of different surface textures patterns based upon the specific design and/or size of the microbeads 24. For example, the surface texture may include points, spikes, spurs, ribs, bumps, ridges, protuberances, etc. which may be configured to project alongside, partially into and/or through the wall of a body lumen, or otherwise engage the wall of a body lumen, thereby providing some degree of interaction (e.g., surface friction, mechanical interlock, interface, engagement, etc.) between the covering composition 20 and the tissue of the body lumen (e.g., esophagus or intestine). The engagement of the textured surface of the covering composition 20 with the tissue of the body lumen may initially prevent stent 10 from longitudinally shifting or migrating with respect to the body lumen upon implantation within the body lumen. In some instances, the covering composition 20 including the surface texture may be configured to remain engaged with the inner surface of the body lumen, thereby not extending into the wall of a body lumen. The covering composition (including a surface texture) may create friction and/or adhesion with the tissue of the body lumen (e.g., the inner surface of the esophagus or intestine), which may prevent stent 10 from longitudinally shifting or migrating with respect to the body lumen. For example, in some instances surface texture may be designed to "grip" the inner surface of a body lumen.

FIG. 5 shows a portion of the example stent 10 deployed in body lumen 50. In particular, FIG. 5 illustrates the covering composition 20 (including the microbeads 24 encapsulated within the covering material 22) and the stent struts 18 forming the expandable scaffold of the stent 10. FIG. 5 shows the stent 10 in an expanded configuration, whereby the roughened surface of the covering composition 20 of the stent 10 is positioned such that it interfaces (e.g., engages) with the inner surface of body lumen 50, thereby providing a resistance to migration of stent 10 within the body lumen 50. For example, FIG. 5 illustrates that one or more microbeads 24 may extend radially outward such that they engage with the inner surface of the body lumen 50. This engagement of the microbeads 24 may effectively lock the covering composition 20 with the inner surface of the body lumen 50, as described above.

It can be appreciated that the covering composition 20 disclosed herein may be configured such that digested material (e.g., digested food, liquids, etc.) cannot pass from an inner surface of the covering composition 20 to the outer surface of the covering composition 20. In other words, when positioned on the outer and/or inner surface of stent 10, the covering composition 20 may define a pathway that permits food to pass through the inner lumen of stent 10 without leaking from the inner surface to the outer surface of the covering composition 20.

As described above, it may be desirable to design a stent which includes both a covered portion and an uncovered portion. It can further be appreciated that designing a stent to include both a covered portion and uncovered portion may allow the stent to be easily removable/repositionable while also reducing the stent's tendency to migrate along a body lumen. In other words, at least some example stent designs disclosed herein may be customized to include both a covered portion and an uncovered portion having particular design parameters (e.g., lengths, coverings/layers, bare sections, etc.) which complement each other to achieve a stent which reduces the tendency of the stent to migrate while also permitting the stent to be readily removable/repositionable should the need arise. FIGS. 7-11 illustrate several example stent designs in which the covering composition covers only a portion of the stent 10.

Figure 7:
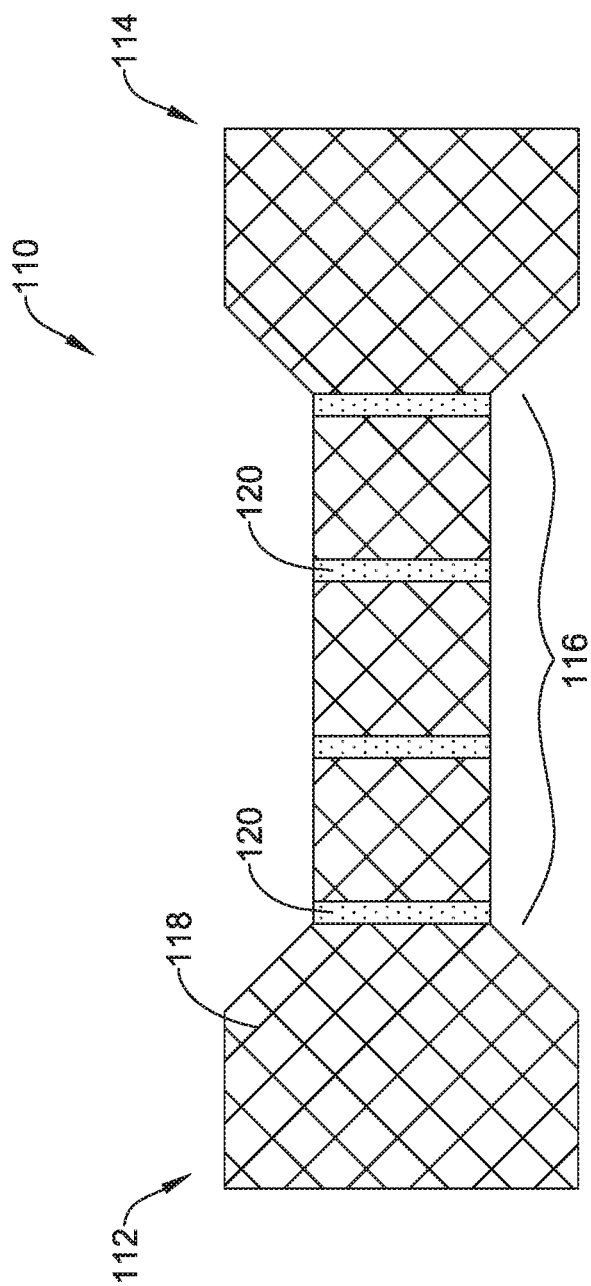
FIG. 7 illustrates another example stent having a covered region and an uncovered region.

For example, FIG. 7 illustrates an example stent 110. The example stent 110 may be similar in form and function to other stent designs described herein. For example, the stent 110 may include a first end region 112, a second end region 114 and a medial region 116 extending between the first end region 112 and the second end region 114. Furthermore, FIG. 7 illustrates the stent 110 having stent struts 118 extending from the first end region 112 to the second end region 114. Similar to stent 10 above, the first end region 112 and/or the second end region 114 may include a flared portion. Additionally, FIG. 7 illustrates that the medial region 116 may include one or more circumferential bands of a covering composition 120 (while the remainder of the stent 110 may be free of the covering composition 120). Further, the covering composition 120 may be similar in form and function to the covering composition 20 described above (including microbeads 24 encapsulated in the coating 22). The covering composition 120 may extend around all or only a portion of the outer surface of the stent 210. As discussed above, the covering composition 120 may be designed to engage with an inner surface of an example body lumen to prevent migration of the stent 110.

Figure 8:
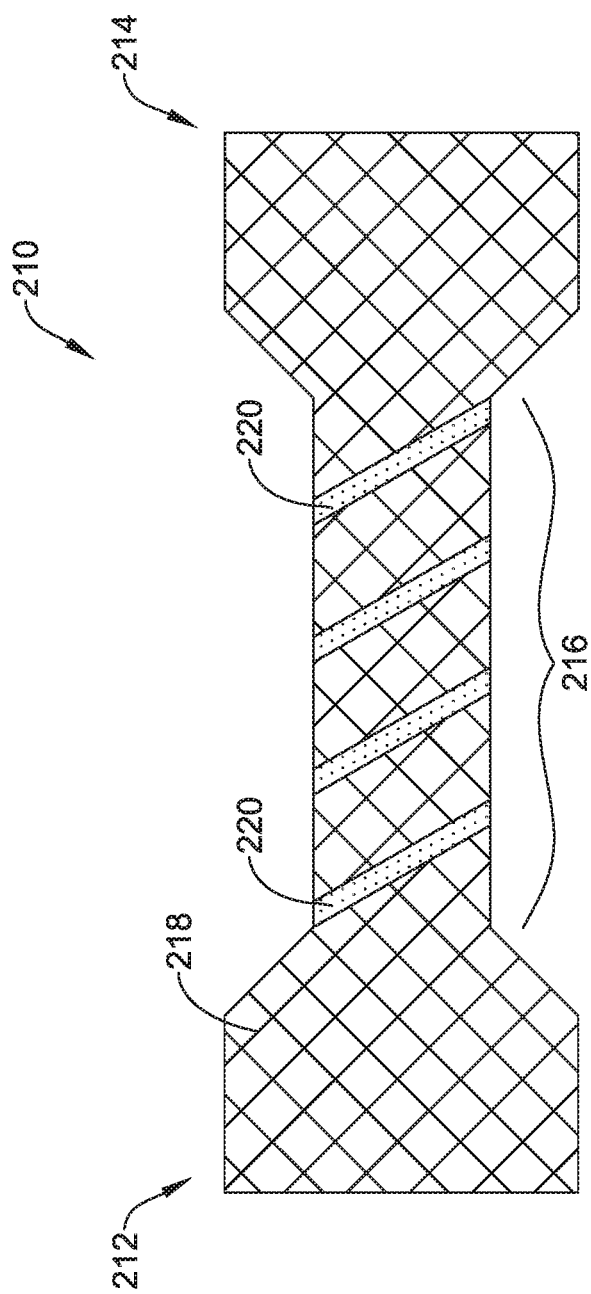
FIG. 8 illustrates another example stent having a covered region and an uncovered region.

FIG. 8 illustrates an example stent 210. The example stent 210 may be similar in form and function to other stent designs described herein. For example, the stent 210 may include a first end region 212, a second end region 214 and a medial region 216 extending between the first end region 212 and the second end region 214. Furthermore, FIG. 8 illustrates the stent 210 having stent struts 218 extending from the first end region 212 to the second end region 214. Similar to stent 10 above, the first end region 212 and/or the second end region 214 may include a flared portion. Additionally, FIG. 8 illustrates that the medial region 216 may include one or more spiral bands of a covering composition 220 (while the remainder of the stent 210 may be free of the covering composition 220). Further, the covering composition 220 may be similar in form and function to the covering composition 20 described above (including microbeads 24 encapsulated in the coating 22). The covering composition 220 may extend around all or only a portion of the outer surface of the stent 210. Additionally, the spiral bands of a covering composition 220 may extend in a right-handed and/or a left-handed direction around the circumference of the stent 210. As discussed above, the covering composition 220 may be designed to engage with an inner surface of an example body lumen to prevent migration of the stent 210.

Figure 9:
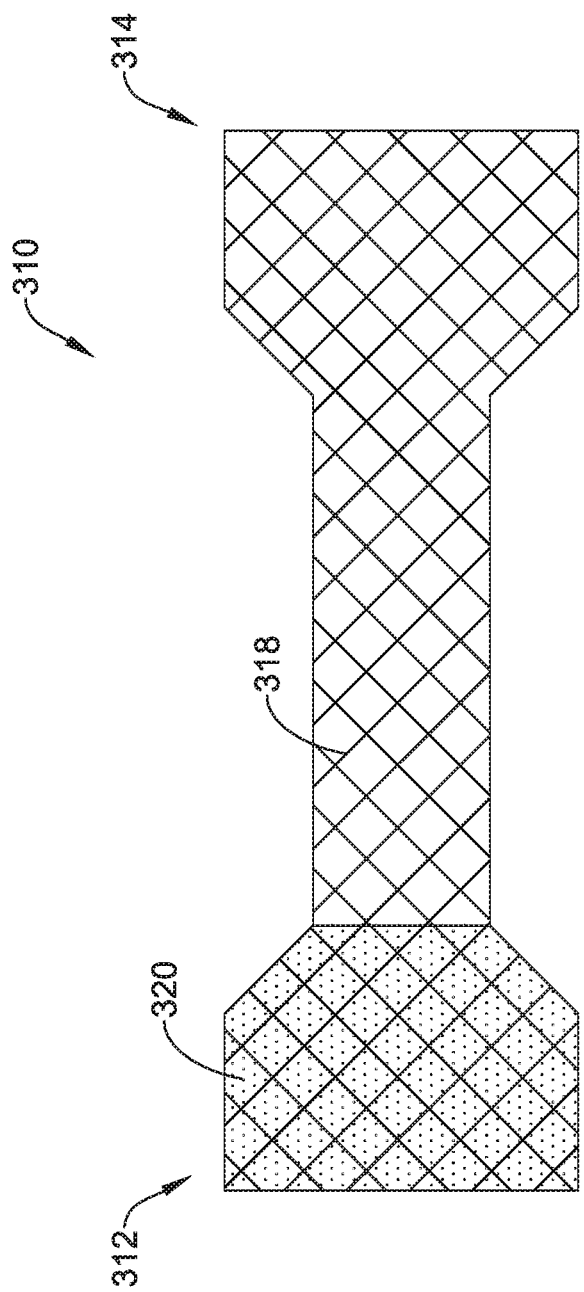
FIG. 9 illustrates another example stent having a covered region and an uncovered region.

FIG. 9 illustrates an example stent 310. The example stent 310 may be similar in form and function to other stent designs described herein. For example, the stent 310 may include a first end region 312, a second end region 314 and a medial region 316 extending between the first end region 312 and the second end region 314. Furthermore, FIG. 9 illustrates the stent 310 having stent struts 318 extending from the first end region 312 to the second end region 314. Similar to stent 10 above, the first end region 312 and/or the second end region 314 may include a flared portion. Additionally, FIG. 9 illustrates that the flared portion of the first end region 312 may include a covering composition 320 (while the remainder of the stent 310 may be free of the covering composition 320). Further, the covering composition 320 may be similar in form and function to the covering composition 20 described above (including microbeads 24 encapsulated in the coating 22). While FIG. 9 shows the covering composition 320 positioned on the first end region 312 of the stent 310, it is contemplated that the covering composition 320 may be positioned on the second end region 314 or both the first end region 312 and the second end region 314 of the stent 310. As discussed above, the covering composition 320 may be designed to engage with an inner surface of an example body lumen to prevent migration of the stent 310.

Figure 10:
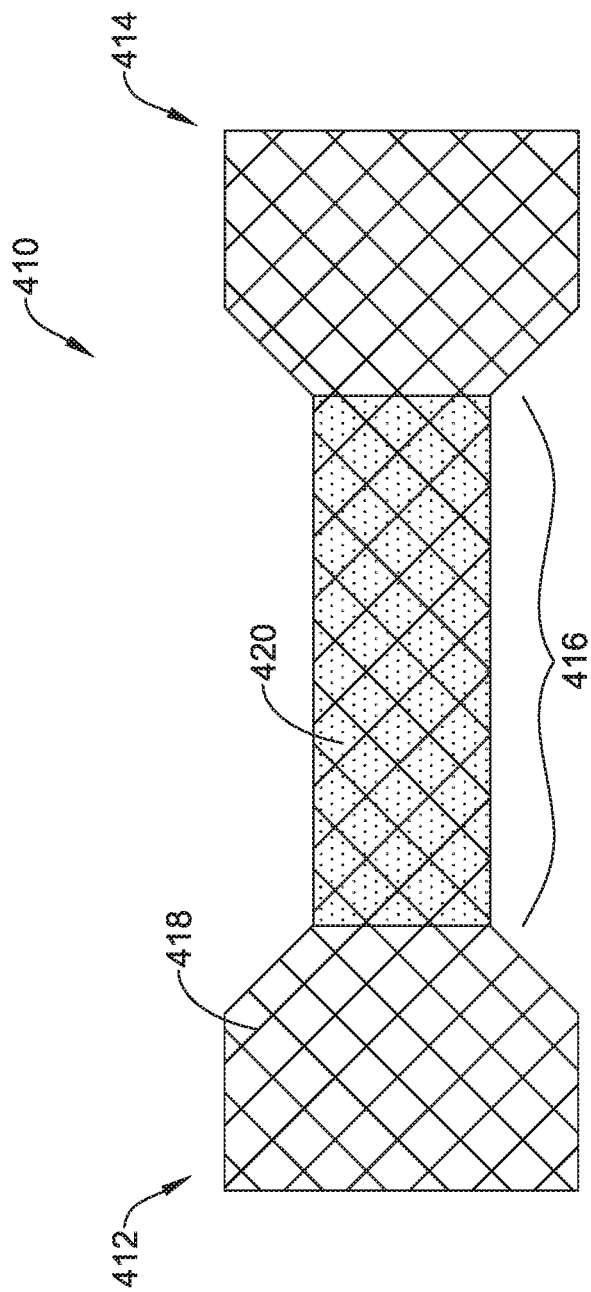
FIG. 10 illustrates another example stent having a covered region and an uncovered region.

FIG. 10 illustrates an example stent 410. The example stent 410 may be similar in form and function to other stent designs described herein. For example, the stent 410 may include a first end region 412, a second end region 414 and a medial region 416 extending between the first end region 412 and the second end region 414. Furthermore, FIG. 10 illustrates the stent 410 having stent struts 418 extending from the first end region 412 to the second end region 414. Similar to stent 10 above, the first end region 412 and/or the second end region 414 may include a flared portion. Additionally, FIG. 10 illustrates that the medial region 416 may include a covering composition 420 (while the remainder of the stent 410 may be free of the covering composition 320). Further, the covering composition 420 may be similar in form and function to the covering composition 20 described above (including microbeads 24 encapsulated in the coating 22). As discussed above, the covering composition 420 may be designed to engage with an inner surface of an example body lumen to prevent migration of the stent 410.

Figure 11:
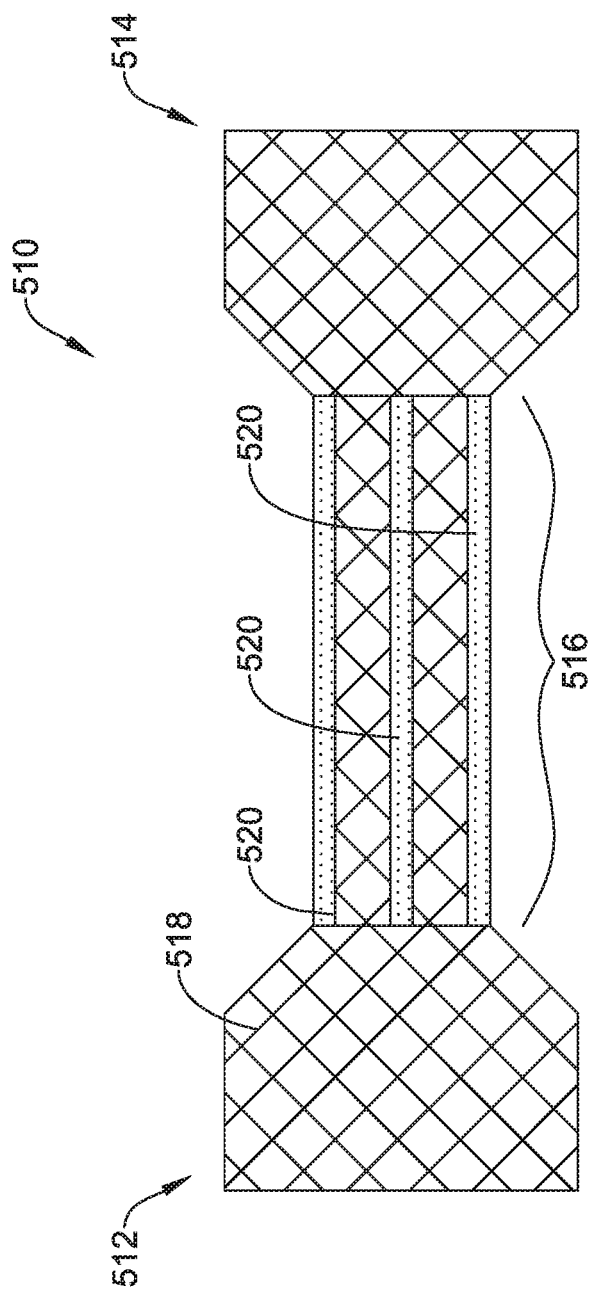
FIG. 11 illustrates another example stent having a covered region and an uncovered region.

FIG. 11 illustrates an example stent 510. The example stent 510 may be similar in form and function to other stent designs described herein. For example, the stent 510 may include a first end region 512, a second end region 514 and a medial region 516 extending between the first end region 512 and the second end region 514. Furthermore, FIG. 11 illustrates the stent 510 having stent struts 518 extending from the first end region 512 to the second end region 514. Similar to stent 10 above, the first end region 512 and/or the second end region 514 may include a flared portion. Additionally, FIG. 11 illustrates that the medial region 516 may include one or more longitudinal strips of the covering composition 520 (while the remainder of the stent 410 may be free of the covering composition 520). Further, the covering composition 520 may be similar in form and function to the covering composition 20 described above (including microbeads 24 encapsulated in the coating 22). As discussed above, the covering composition 520 may be designed to engage with an inner surface of an example body lumen to prevent migration of the stent 510.

Additionally, it is contemplated that the covering composition 20 (and related variations thereof) may be formed by utilizing a spray coating process to layer the coating 22 on the surface of the stent 10. Furthermore, this spray coating process may be utilized to encapsulate the microbeads 24 within or along the coating 22. For example, in some cases, the stent 10 may be sprayed coated with the one or more substrate layers of the coating material 22. The substrate layers of the coating material may fully or partially cover the stent struts 18, as described above. After the initial substrate layers have been applied to the stent 10, a plurality of microbeads may be applied to the uncured substrate layer of coating 22. After the microbeads 24 have been applied to the uncured substrate layer of coating material 22, one or more top-coat layers of the coating material 22 may be applied to the stent 10 to fully encapsulate the microbeads 24 within the coating material 22. Additionally, in some examples, another layer of microbeads 24 may be applied to the uncured top-coat layers of the coating material 22 of stent 10, whereby a portion of some of the microbeads 24 is not encapsulated by the coating material 22. In yet other examples, the microbeads 24 may only be applied to the outer surface of the coating material 22, whereby no microbeads are fully encapsulated in the coating material 22. While the above description discloses application of the coating material utilizing a spray-coating process, other application processes are contemplated. For example, stent 10 may be constructed using a dip coating process, etc.

The materials that can be used for the various components of stent 10 (and/or other stents disclosed herein) and the various tubular members disclosed herein may include those commonly associated with medical devices. For simplicity purposes, the following discussion makes reference to stent 10 (and/or other stents disclosed herein) and other components of stent 10 (and/or other stents disclosed herein). However, this is not intended to limit the devices and methods described herein, as the discussion may be applied to other similar tubular members and/or components of tubular members or devices disclosed herein.

Stent 10 (and/or other stents disclosed herein) and/or other components of stent 10 (and/or other stents disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent 10 (and/or other stents disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10 (and/or other stents disclosed herein) in determining its location. Some examples of radiopaque materials can include, but are not limited to, gold, platinum, palladium, tantalum, tungsten alloy, polymer material loaded with radiopaque filler, and the like. Additionally, other radiopaque marker bands and/or coils may also be incorporated into the design of stent 10 (and/or other stents disclosed herein) to achieve the same result.

In some embodiments, a degree of Magnetic Resonance Imaging (MRI) compatibility is imparted into stent 10 (and/or other stents disclosed herein). For example, stent 10 (and/or other stents disclosed herein), or portions thereof, may be made of a material that does not substantially distort the image and create substantial artifacts (e.g., gaps in the image). Certain ferromagnetic materials, for example, may not be suitable because they may create artifacts in an MRI image. Stent 10 (and/or other stents disclosed herein), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device for treating a body lumen, comprising:
   an expandable scaffold including a first end region, a second end region opposite the first end region and an outer surface;
   a polymeric covering disposed along the outer surface of the expandable scaffold, the covering having an outer surface, wherein the polymeric covering is not biodegradable; and
   a plurality of granular particles disposed along the covering, wherein the granular particles comprise at least a first microbead having a first outer diameter, and wherein the first outer diameter is between 0.5 mm and 0.9 mm wherein adjacent ones of the plurality of granular particles are stacked radially outward from the outer surface of the expandable scaffold one on top of another;
   wherein the expandable scaffold is configured to shift from a collapsed state to an expanded state;

wherein the covering is configured to contact an inner surface of the body lumen in the expanded state;

wherein the granular particles are designed to prevent migration of the expandable scaffold upon implantation in the body lumen.

2. The medical device of claim 1, wherein at least some of the plurality of granular particles are encapsulated within the covering.

3. The medical device of claim 2, wherein some of the granular particles are disposed along the outer surface of the covering.

4. The medical device of claim 1, wherein the first microbead is spherically-shaped.

5. The medical device of claim 1, further comprising a second microbead, and wherein the second microbead extends radially outward from the outer surface of the expandable scaffold a greater distance than the first microbead extends from the outer surface of the expandable scaffold.

6. The medical device of claim 1, wherein the expandable scaffold includes a plurality of interstices located therein, and wherein the covering spans at least one of the plurality of interstices.

7. The medical device of claim 1, wherein the plurality of granular particles are arranged to create a surface texture having a variable surface roughness.

8. The medical device of claim 1, wherein the covering includes a first thickness and a second thickness different from the first thickness.

9. The medical device of claim 1, wherein the first end region, the second end region or both the first end region and the second end region include a flared portion.

10. The medical device of claim 1, wherein the covering is disposed along the entire outer surface of the expandable scaffold.

11. A medical device for treating a body lumen, comprising:
an expandable scaffold including a first end region, a second end region opposite the first end region and an outer surface;
a polymeric covering disposed along the outer surface of the expandable scaffold, wherein the polymeric covering is not biodegradable; and
a plurality of microbeads disposed along the covering, the microbeads having a first outer diameter between 0.50 mm and 0.90 mm;
wherein the plurality of microbeads are disposed along the covering to form a variable surface texture, wherein adjacent ones of the plurality of microbeads are stacked radially outward from the outer surface of the expandable scaffold one on top of another;
wherein the covering is configured to contact an inner surface of the body lumen such that the plurality of microbeads prevent migration of the expandable scaffold upon implantation in the body lumen.

12. The medical device of claim 11, wherein the plurality of microbeads are encapsulated within the covering.

13. The medical device of claim 11, wherein at least some of the plurality of microbeads are spherically-shaped.

14. The medical device of claim 11, wherein the plurality of microbeads includes a first microbead and a second microbead, and wherein the second microbead extends radially outward from the outer surface of the expandable scaffold a greater distance than the first microbead extends from the outer surface of the expandable scaffold.

15. The medical device of claim 11, wherein the covering includes a first thickness and a second thickness different from the first thickness.

16. A medical device for treating a body lumen, comprising:
an expandable scaffold including a first end region, a second end region opposite the first end region and an outer surface;
a polymeric covering disposed along the outer surface of the expandable scaffold, the covering having an outer surface, wherein the polymeric covering is not biodegradable; and
a plurality of granular particles disposed along the covering, wherein the granular particles comprise at least a first microbead having a first outer diameter, and wherein the first outer diameter is between 0.5 mm and 0.9 mm, and wherein adjacent ones of the plurality of granular particles are stacked radially outward from the outer surface of the expandable scaffold one on top of the other wherein a first portion of the granular particles are fully embedded within the covering and a second portion of the granular particles extend radially outward from the outer surface of the polymeric covering;
wherein the expandable scaffold is configured to shift from a collapsed state to an expanded state;
wherein the covering is configured to contact an inner surface of the body lumen in the expanded state;
wherein the granular particles are designed to prevent migration of the expandable scaffold upon implantation in the body lumen.

* * * * *